(12) United States Patent
Kondo et al.

(10) Patent No.: US 10,099,345 B2
(45) Date of Patent: Oct. 16, 2018

(54) BLAST TREATMENT DEVICE AND BLAST TREATMENT METHOD

(71) Applicant: FUJI JUKOGYO KABUSHIKI KAISHA, Tokyo (JP)

(72) Inventors: Yoshihiko Kondo, Tochigi (JP); Hirotsugu Takazawa, Tochigi (JP); Shinya Matsuo, Tokyo (JP); Tatsuo Nakahata, Tokyo (JP); Osamu Shibasaki, Tokyo (JP); Ryohei Ono, Tokyo (JP)

(73) Assignee: SUBARU CORPORATION, Tokyo (JP)

( * ) Notice: Subject to any disclaimer, the term of this patent is extended or adjusted under 35 U.S.C. 154(b) by 196 days.

(21) Appl. No.: 14/828,848

(22) Filed: Aug. 18, 2015

(65) Prior Publication Data

US 2016/0059382 A1 Mar. 3, 2016

(30) Foreign Application Priority Data

Aug. 28, 2014 (JP) ................................ 2014-174130

(51) Int. Cl.
*B24B 1/00* (2006.01)
*B24C 1/06* (2006.01)
(Continued)

(52) U.S. Cl.
CPC .................. *B24C 1/06* (2013.01); *B24C 3/32* (2013.01); *B24C 7/0053* (2013.01); *B24C 11/00* (2013.01); *G01B 5/30* (2013.01); *G01N 3/08* (2013.01)

(58) Field of Classification Search
CPC ........... B24C 1/06; B24C 3/32; B24C 7/0053; B24C 11/00; G01B 5/30; G01N 3/08
See application file for complete search history.

(56) References Cited

U.S. PATENT DOCUMENTS

| 2,350,440 A | 6/1944 | Almen |
|---|---|---|
| 7,210,322 B2 | 5/2007 | Iwata |

(Continued)

FOREIGN PATENT DOCUMENTS

| CN | 1688413 | 10/2005 |
|---|---|---|
| CN | 102341217 | 2/2012 |

(Continued)

OTHER PUBLICATIONS

Extended European search report dated Jan. 28, 2016, in Patent Application No. 15 182 505.6 (9 pages).

(Continued)

*Primary Examiner* — Timothy V Eley
(74) *Attorney, Agent, or Firm* — Smith, Gambrell & Russell, LLP

(57) ABSTRACT

According to one implementation, a blast treatment method includes: setting a blast treatment condition for a composite material to make a degree of activation on the surface of the composite material within an appropriate range, based on reference information; and manufacturing a blast treated product by the blast treatment of the composite material under the blast treatment condition set to make the degree of the activation within the appropriate range. The reference information shows a relation between a strain amount of a test piece caused by blast treatment under a predetermined blast treatment condition and a degree of activation on a surface of a sample of a composite material by blast treatment, for activating the surface of the sample before painting or bonding, under the predetermined blast treatment condition.

15 Claims, 8 Drawing Sheets

(51) Int. Cl.
  *B24C 3/32* (2006.01)
  *B24C 7/00* (2006.01)
  *B24C 11/00* (2006.01)
  *G01B 5/30* (2006.01)
  *G01N 3/08* (2006.01)

(56) References Cited

U.S. PATENT DOCUMENTS

| | | |
|---|---|---|
| 9,289,880 B2 | 3/2016 | Yamada et al. |
| 2009/0092849 A1 | 4/2009 | Oguri et al. |
| 2009/0107629 A1 | 4/2009 | Oguri |
| 2009/0266331 A1 | 10/2009 | Ando |
| 2013/0074305 A1 | 3/2013 | Tolentino |

FOREIGN PATENT DOCUMENTS

| | | |
|---|---|---|
| JP | H04-13573 A | 1/1992 |
| JP | H06-246637 A | 9/1994 |
| JP | H08-302425 A | 11/1996 |
| JP | 2007-244980 A | 9/2007 |
| JP | 2007-277601 A | 10/2007 |
| JP | 2009-264236 A | 11/2009 |
| JP | 2013-215826 | 10/2013 |

OTHER PUBLICATIONS

Marvin B Happ et al.,"Almen Strip Variability—A Statistical Treatment", The Shot Peener, Dec. 31, 1996, pp. 1-10.
Japanese Office Action dated Apr. 3, 2018 in Japanese Patent Application No. 2014-174130 (3 pages in Japanese, and English machine translation).
First Chinese Office Action dated Jul. 26, 2018 in Chinese Patent Application No. 201510542146.3 (11 pages).

| TYPE | THICKNESS [mm] | HARDNESS | FLATNESS [mm] |
|---|---|---|---|
| TYPE A | 1.27~1.32 | 44 HRC~50 HRC | 0.025 |
| TYPE C | 2.36~2.41 | 44 HRC~50 HRC | 0.038 |
| TYPE N | 0.76~0.81 | 72.5 HRA~76 HRA | 0.025 |
| TYPE H | 1.27~1.32 | 58 HRC~62 HRC | 0.025 |
| TYPE T | 0.51~0.54 | 73.5 HRA~75.9 HRA | 0.025 |

FIG. 4

| NOZZLE DISTANCE [mm] | THE NUMBER OF INJECTION(S) | BLAST PRESSURE [MPa] | | | | | |
|---|---|---|---|---|---|---|---|
| | | 0.1 | 0.2 | 0.3 | 0.4 | 0.5 | 0.6 |
| 200 | 1 | PASS | PASS | PASS | PASS | PASS | PASS |
| | 2 | PASS | PASS | PASS | NG | NG | NG |
| | 3 | PASS | PASS | NG | NG | NG | NG |
| 280 | 1 | PASS | PASS | PASS | PASS | PASS | PASS |
| | 2 | PASS | PASS | PASS | PASS | PASS | NG |
| | 3 | PASS | PASS | PASS | NG | NG | NG |

FIG. 6

BLAST TREATMENT DEVICE AND BLAST TREATMENT METHOD

CROSS REFERENCES TO RELATED APPLICATIONS

This application is based upon and claims the benefit of priority from Japanese Patent Application No. 2014-174130, filed on Aug. 28, 2014; the entire contents of which are incorporated herein by reference.

FIELD

Implementations described herein relate generally to a blast treatment device and a blast treatment method.

BACKGROUND

Conventionally, in case of painting or bonding a composite material, such as GFRP (glass fiber reinforced plastics) or CFRP (carbon fiber reinforced plastics), which is used as a material of aircraft parts or the like, a blast treatment as a pretreatment is performed for the surface of the composite material (for example, refer to Japanese Patent Application Publication No. 2013-215826).

When blast treatment is performed, a surface of a composite material is activated. Specifically, surface roughness of the composite material becomes large, and a surface energy of the composite material becomes larger than an interface energy between the composite material and a paint. As a result, the wettability of a paint or an adhesive on the composite material is improved, and it becomes possible to prevent a paint peeling and an adhesive imperfection.

Whether the blast treatment has activated the surface of the composite material sufficiently to be appropriate for painting or bonding is evaluated through a visual observation by an examiner or measurement of a surface roughness of the composite material.

An object of the present invention is to provide a blast treatment device and a blast treatment method which can obtain a composite material whose surface has been activated with a more satisfactory quality by blast treatment of the composite material before painting or bonding.

SUMMARY OF THE INVENTION

In general, according to one implementation, a blast treatment method includes: setting a blast treatment condition for a composite material, which is a target of blast treatment for activating a surface before painting or bonding, to make a degree of activation on the surface of the composite material within an appropriate range, based on reference information; and manufacturing a blast treated product by the blast treatment of the composite material, which is the target of the blast treatment, under the blast treatment condition set to make the degree of the activation within the appropriate range. The reference information shows a relation between a strain amount of a test piece caused by blast treatment under a predetermined blast treatment condition and a degree of activation on a surface of a sample of a composite material by blast treatment, for activating the surface of the sample before painting or bonding, under the predetermined blast treatment condition.

Further, according to one implementation, a blast treatment method includes: manufacturing a blast treated product by blast treatment of a test piece and a composite material, which is a target of the blast treatment for activating a surface before painting or bonding, under a same blast treatment condition; measuring a strain amount of the test piece after the blast treatment; and evaluating whether a degree of activation on the surface of the composite material after the blast treatment is within an appropriate range, based on a measurement result of the strain amount and reference information. The reference information shows a relation between a strain amount of the test piece or another test piece caused by blast treatment under a predetermined blast treatment condition and a degree of activation on a surface of a sample of a composite material by blast treatment, for activating the surface of the sample before painting or bonding, under the predetermined blast treatment condition.

Further, according to one implementation, a blast treatment method includes: setting blast treatment condition under which an arc height value of a T strip of an Almen strip or a test piece, which can be considered to be substantially equivalent to the T strip, becomes from 0.05 mm to 0.12 mm by blast treatment; and manufacturing a blast treated product by blast treatment of a composite material, which is a target of the blast treatment for activating a surface before painting or bonding, under the blast treatment condition.

Further, according to one implementation, a blast treatment device includes storage circuitry, processing circuitry and blasting structure. The storage circuitry stores reference information showing a relation between a strain amount of a test piece caused by blast treatment under a predetermined blast treatment condition and a degree of activation on a surface of a sample of a composite material by blast treatment for activating the surface before painting or bonding under the predetermined blast treatment condition. The processing circuitry is configured to set a blast treatment condition for a composite material, which is a target of blast treatment for activating a surface before painting or bonding, to make a degree of activation on the surface of the composite material, which is the target of the blast treatment, within an appropriate range, based on the reference information. The blasting structure is configured to perform the blast treatment of the composite material, which is the target of the blast treatment, under the blast treatment condition determined to make the degree of the activation within the appropriate range.

BRIEF DESCRIPTION OF THE DRAWINGS

In the accompanying drawings:

FIG. 4 shows types of the Almen strip shown in FIG. 2;

FIG. 6 shows an example of results of good or bad in a degree of activation of a blast treated surface of a sample of CFRP with changing blast treatment conditions;

DETAILED DESCRIPTION

A blast treatment device and a blast treatment method according to implementations of the present invention will be described with reference to the accompanying drawings.
(Structure and Function)

Figure 1:
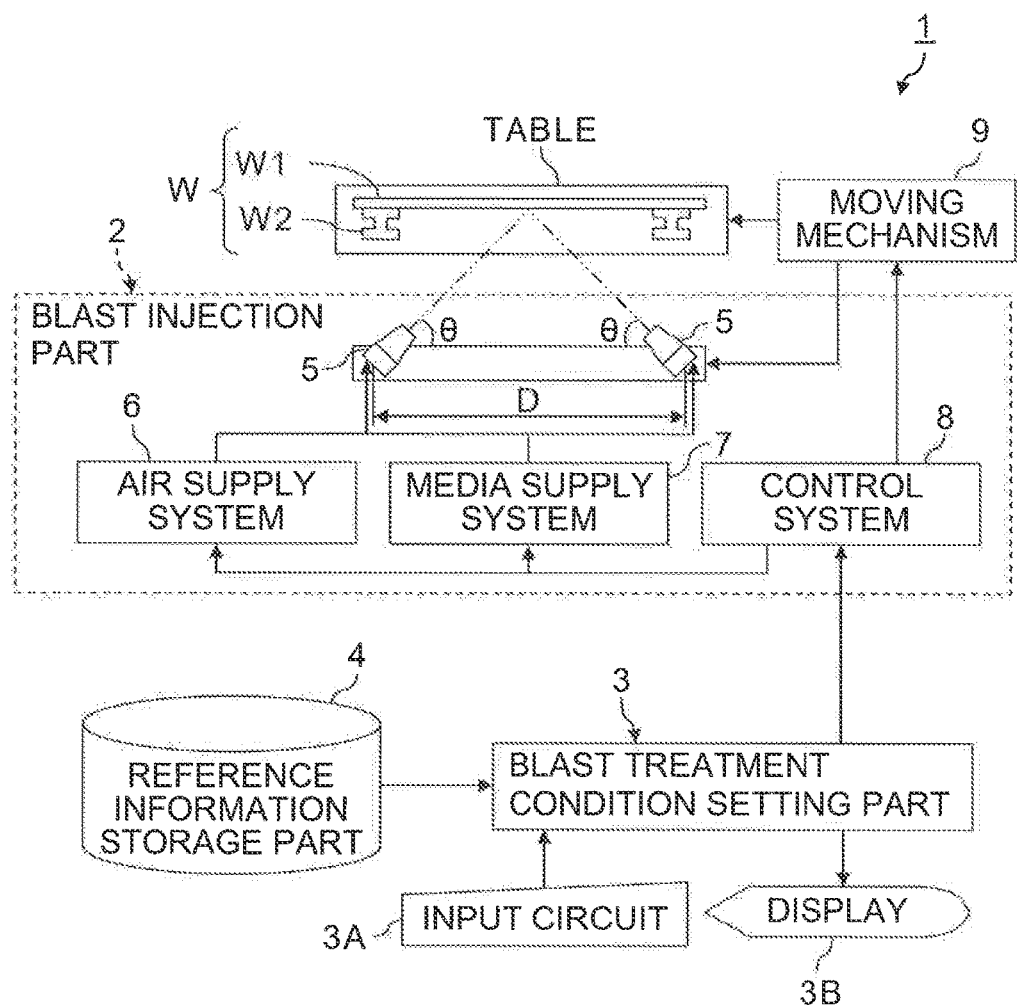
FIG. 1 is a configuration diagram of a blast treatment device according to an implementation of the present invention.

FIG. 1 is a configuration diagram of a blast treatment device according to an implementation of the present invention.

A blast treatment device 1 performs a blast treatment for activating a surface, before painting or bonding, of a workpiece W made with a composite material, such as CFRP or GFRP. Specifically, the blast treatment device 1 performs a shot blast treatment by making projection materials, consisting of particles, serving as media, collide on the workpiece W to roughen the surface of the workpiece W. Thereby, the wettability of a paint or an adhesive can be improved. As the media for blast treatment of the composite material, hard particles, such as ceramic, are typical. More specifically, ceramic particles, such as alumina, silica, silicon carbide or zirconia particles, can be used as the media for blast treatment.

The blast treatment device 1 has a blast injection part 2, a blast treatment condition setting part 3 and a reference information storage part 4. The blast treatment condition setting part 3 can be configured by processing circuitry such as a computer. Specifically, the blast treatment condition setting part 3 can be configured by an operation circuit executing programs stored in a storage or an operation circuit executing programs stored precedently in itself. Meanwhile, the reference information storage part 4 can be configured by storage circuitry.

The blast injection part 2 is blasting structure configured to perform a blast treatment of the workpiece W under set blast treatment conditions. For that purpose, the blast injection part 2 has at least one nozzle 5 for injecting media of blast treatment to the workpiece W, an air supply system 6 for supplying compressed air to the nozzle 5 or the nozzles 5, a media supply system 7 for supplying the media to the nozzle 5 or the nozzles 5, and a control system 8 for controlling each element of the blast treatment device 1 according to blast treatment conditions. The control system 8 can be configured by processing circuitry executing programs stored in a storage or processing circuitry executing programs stored precedently in itself, to which signal cables for transmitting control signals have been coupled. The control system 8 may be integrated with the blast treatment condition setting part 3.

In the example shown in FIG. 1, the workpiece W, configured by attaching stringers W2 on a panel W1 made with a composite material, has been placed on a table, and the two nozzles 5 are installed in the blast injection part 2 so that the media can be simultaneously injected toward a blast treatment position of the workpiece W from different directions.

Furthermore, the blast treatment device 1 can have a moving mechanism 9 for moving at least one of the workpiece W and the nozzles 5 so that the relative position of the nozzles 5 and the workpiece W can be changed. It is practical to allow moving at least one of the workpiece W and the nozzles 5 in three-axis directions by the moving mechanism 9. The moving mechanism 9 can have an arbitrary structure. For example, the moving mechanism 9 can adopt, as elements, a structure to move at least one of the workpiece W and the nozzles 5 in arbitrary axis directions along rails or a linkage mechanism, such as a multijoint arm, to move at least one of the workpiece W and the nozzles 5. In this case, the relative position, between the nozzles 5 and the workpiece W, including a distance therebetween is one of the blast treatment conditions. Therefore, the blast treatment device 1 is configured so as to control the moving mechanism 9 by the control system 8.

The blast treatment condition setting part 3 is coupled to an input circuit 3A and a display 3B. The blast treatment condition setting part 3 has a function to set the blast treatment conditions according to information input by operating the input circuit 3A. Meanwhile, the reference information storage part 4 stores reference information referred to for setting the blast treatment conditions as appropriate conditions.

Thus, the blast treatment condition setting part 3 has a function to set the blast treatment conditions for a composite material, which is a target of blast treatment for activating a surface before painting or bonding, so as to make a degree of activation on the surface of the composite material within an appropriate range, based on the reference information stored in the reference information storage part 4. Therefore, the blast injection part 2 can perform a blast treatment of the composite material, which is a target of the blast treatment, under the blast treatment conditions determined so that the degree of activation on the surface becomes within an appropriate range.

The reference information referred to in order to set appropriate blast treatment conditions is stored in the reference information storage part 4, as information showing a relation between an amount of strain (an amount of deformation) of a test piece, whose form is known, caused by a blast treatment under predetermined blast treatment conditions, and the degree of activation on the surface of a sample of the composite material, in case of performing a blast treatment of the sample under the same predetermined blast treatment conditions.

Specifically, strain amounts of the test piece by blast treatments under different blast treatment condition sets can be related with the corresponding blast treatment condition sets respectively. Similarly, degrees of activation on a surface of a sample of composite material by blast treatments under the blast treatment condition sets same as those to the test piece can be related with the corresponding blast treatment condition sets respectively. Then, the degree of activation on the surface of the composite material can be associated with the strain amount of the test piece, for every blast treatment condition set. As a result, the degree of activation on the surface of the composite material can be expressed quantitatively using the strain amount of the test piece as an index.

Therefore, an appropriate range of degree of activation on surface of a composite material can be obtained as a range of strain amount of a test piece, by testing blast treatments of the test piece and a sample of the composite material under the same blast treatment condition sets. Then, blast treatment conditions corresponding to the range of the strain amount of the test piece, corresponding to the appropriate range of the degree of activation on the surface of the composite material, are to be appropriate conditions.

In particular, when a degree of activation on a surface of a composite material is expressed quantitatively using a strain amount of a test piece as an index, more appropriate blast treatment conditions can be easily set by referring to a strain amount of the test piece, in order to obtain a required degree of the activation. Furthermore, in case of performing a blast treatment of a test piece together with a composite material which is a target of the blast treatment, a measurement result of a strain amount of the test piece can be recorded as an inspection record showing a quality of the composite material after the blast treatment. That is, a degree of activation on a surface of a composite material after a blast treatment can be quantitatively evaluated as a numerical value, by referring to a measurement result of a strain amount of a test piece.

On the other hand, also in case of not performing a blast treatment of a test piece, a strain amount of the test piece corresponding to blasting conditions can be recorded as an inspection record showing a quality of a composite material after a blast treatment. In this case, it is possible to quantitatively estimate a degree of activation on a surface of the composite material after the blast treatment easily, by referring to the strain amount of the test piece corresponding to the blasting conditions.

Furthermore, accumulating measurement results of strain amounts of test pieces and statistically evaluating a dispersion make it possible to evaluate not only a composite material but also performance, such as a control error, of the blast treatment device 1. Therefore, a measurement result of a strain amount of a test piece can be recorded as an inspection record of at least one of a composite material after a blast treatment and the blast treatment device 1 used for a blast treatment.

Furthermore, it is also possible to evaluate performance, such as a control error, of the blast treatment device 1 by comparing a measurement result of a strain amount of a test piece with a strain amount of the test piece corresponding to set blast treatment conditions. Therefore, a strain amount of a test piece corresponding to set blast treatment conditions can also be recorded as an inspection record of at least one of a composite material after a blast treatment and the blast treatment device 1 used for a blast treatment.

As a test piece, which is a target of blast treatment, an arbitrary form and material can be adopted as long as strain amounts can be measured in appropriate accuracy in case of performing blast treatments with changing blast treatment conditions. An example of the test piece with especially high versatility and practicality is an Almen strip.

Originally, an Almen strip is a test piece standardized for shot peening of a spring or a gear. The shot peening is a surface treatment, for improving a fatigue strength or a stress corrosion cracking resistance, by applying a residual compressive stress on a surface of a metal. Specifically, when plastic working is performed on a surface of a metal by the shot peening, a compressive residual stress is applied to a surface layer of the metal by a work hardening. As a result, mechanical characteristics of the metal, such as a spring or a gear, can be improved.

An Almen strip is a metal piece used for measuring a peening intensity of shot peening of a metal. Note that, the peening intensity is a kinetic energy of shots acting on a unit surface area of a metal, which is a target of the shot peening, per unit time.

Figure 2:
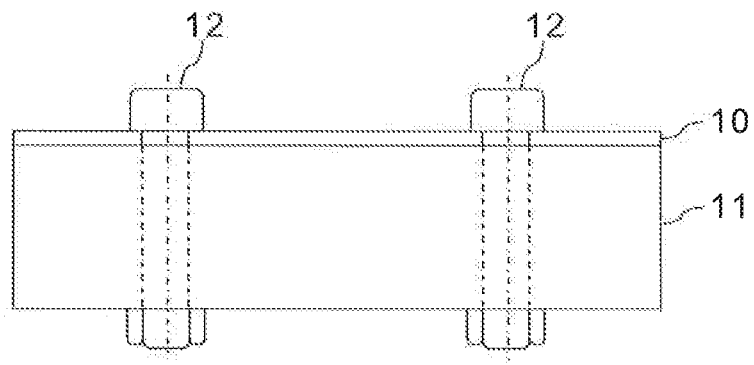
FIG. 2 is a front view of an Almen strip held by an Almen holder.
Figure 3:
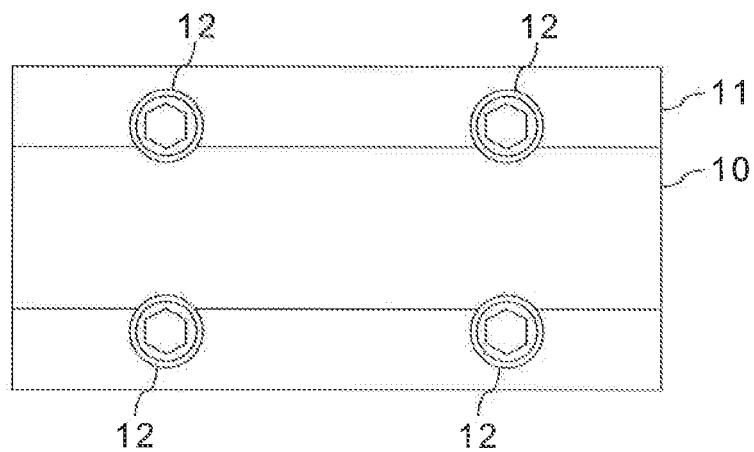
FIG. 3 is a top view of the Almen holder and the Almen strip shown in FIG. 2.

FIG. 2 is a front view of an Almen strip held by an Almen holder, and FIG. 3 is a top view of the Almen holder and the Almen strip shown in FIG. 2.

As shown in FIG. 2 and FIG. 3, an Almen strip 10 has a rectangular and platy form. The Almen strip 10 is used in the state where the Almen strip 10 is fixed to a standardized and specialized Almen holder 11 by four screws 12. Namely, the Almen strip 10 held by the Almen holder 11 is attached to a metal which is a target of shot peening. Then, shot peening of the Almen strip 10 together with the metal is performed.

FIG. 4 shows types of the Almen strip 10 shown in FIG. 2.

The kinds, such as an A strip, a C strip, an N strip, an H strip and a T strip, differing in thickness, hardness or flatness have been prepared as the Almen strip 10. Note that, a width of the Almen strip 10 is 19.0 (+0, −0.1) mm, regardless of the kinds, and a length of the Almen strip 10 is 76.0±0.4 mm, regardless of the kinds.

The hardness of the Almen strip 10 is defined by the Rockwell hardness as a unit. The Rockwell hardness includes plural scales, such as HRA and HRC. The HRA, which is used as the unit of hardness of the Almen strip 10, is a scale for measuring hardness with applying 60 kg of a test load on a diamond conical indenter whose tip radius is 0.2 mm and whose tip angle is 120 degrees. Meanwhile, the HRC is a scale for measuring hardness with applying 150 kg of a test load on a diamond conical indenter whose tip radius is 0.2 mm and whose tip angle is 120 degrees. In both cases of the HRA and the HRC, a Rockwell hardness value HR can be obtained by HR=100-500 h, wherein h represents a permanent depth from a reference surface. As a material of the Almen strip 10, a carbon steel containing 0.60%-0.90% carbon is used. Examples of a carbon steel containing 0.60%-0.90% carbon includes a carbon tool steel, such as SK65M-SK85M, and a spring steel, such as SUP3.

Note that, detailed matters, such as tolerance or a material, may be revised. Furthermore, detailed matters may be different among manufacturers of the Almen strip 10, and nominal designation of a similar kind of the Almen strip 10 may also be different among manufacturers.

Figure 5:
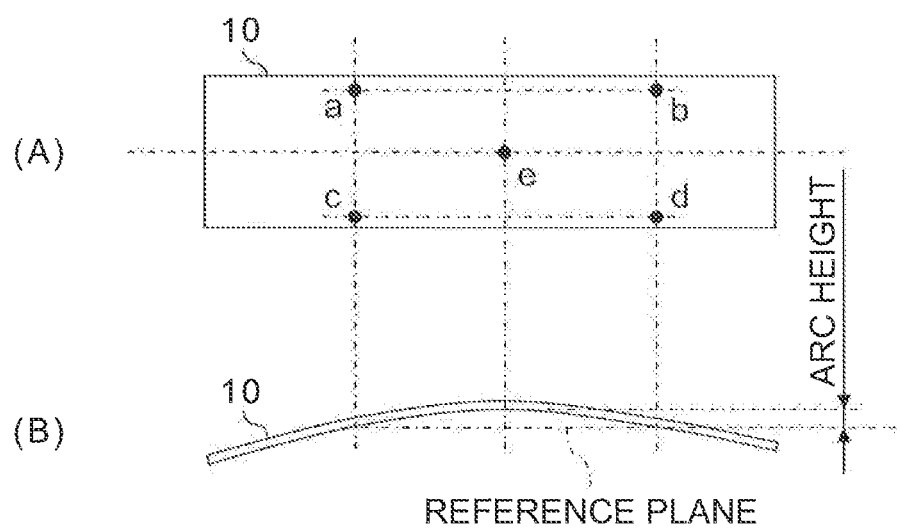
FIG. 5 shows a definition of arc height of the Almen strip shown in FIG. 2.

FIG. 5 shows a definition of arc height of the Almen strip 10 shown in FIG. 2.

(A) of FIG. 5 is a bottom view of the Almen strip 10 of which shot peening has been applied on the top face side, and (B) of FIG. 5 is a front view of the Almen strip 10 shown in (A) of FIG. 5.

When shot peening is applied to the Almen strip 10, the Almen strip 10 deforms by a residual stress. An amount of deformation of the Almen strip 10, caused by applying the shot peening on one side of the Almen strip 10, is called arc height. As shown in FIG. 5, the arc height is defined as height from the reference plane at the midpoint e of four points a, b, c and d, each defined to be on the reference plane, each located on a curved surface of the Almen strip 10 on which shot peening is not applied, and having predetermined intervals.

The four points a, b, c and d are determined to lie the vertices of a rectangle. The distance between a and c and the distance between b and d are 15.88±0.05 [mm] while the distance between a and b and the distance between c and d are 31.75±0.05 [mm]. The tolerance of the distance between the midpoint e and each other point is ±0.1 [mm]. Note that, these numeric definitions may be revised.

Arc height shows a value according to a compressive residual stress in a surface layer of the Almen strip 10. Therefore, peening intensity can be indirectly shown using the arc height. Note that, mechanical characteristics of a metal, to which shot peening has been applied, also depend on a size, a form, and hardness of shots besides the peening intensity.

Arc height can be measured by a marketed Almen gauge. An Almen gauge is a dedicated measuring instrument used for measuring the arc height of the Almen strip 10. A typical Almen gauge has four balls contacting with the curved Almen strip 10 at the four points a, b, c and d respectively, and a contact type feeler for measuring the height from the reference plane at the midpoint e of the curved Almen strip 10.

As described above, the Almen strip 10 is originally a test piece used in order to evaluate peening intensity for obtaining desired mechanical characteristics of a metal, by measuring arc height according to a residual compressive stress. However, the Almen strip 10 can also be used as a test piece for quantifying a degree of activation of a surface of a composite material, due to blast treatment, before painting or bonding. Specifically, a characteristic of a surface of a composite material which influences on a degree of activation of the surface of the composite material, such as surface roughness, can be indirectly shown as a numerical value by the arc height of the Almen strip 10 according to a residual compressive stress.

Note that, a test piece which has not been marketed as the Almen strip 10 can also be used as a test piece for quantifying a degree of activation of a surface of a composite material before painting or bonding as long as the test piece can be considered to be substantially equivalent to the Almen strip 10.

Therefore, the Almen strip 10 or a test piece which can be considered to be substantially equivalent to the Almen strip 10 can be used as a test piece for quantifying a degree of activation of a surface of a composite material before painting or bonding. Then, an arc height value of the Almen strip 10 or the test piece, which can be considered to be substantially equivalent to the Almen strip 10, can be a strain amount of the test piece, which should be related with the degree of activation of the surface of the composite material before painting or bonding.

In case of blast treatment of a composite material, particulates, such as alumina, which are different from media for shot peening of a metal are used as media. Accordingly, the T strip, which is the Almen strip 10 for particulate shots, or a test piece, which can be considered to be substantially equivalent to the T strip, can be used as a test piece for quantifying a degree of activation of a surface of a composite material before painting or bonding. The T strip is the Almen strip 10 defined as one whose Rockwell hardness is 74.7±1.2 HRA, thickness is from 0.51 mm to 0.54 mm, flatness is ±0.025 mm, width is 19.0 (+0, −0.1) mm and length is 76.0±0.4 mm.

As described above, using an existing test piece standardized for a different purpose allows omitting to make a new standard. Thereby, it becomes possible to indirectly measure a degree of activation of a surface of a composite material before painting or bonding, using an existing measuring instrument, such as an Almen gauge. Therefore, even in case of using a test piece belonging to an arbitrary standard, other than the Almen strip 10, a degree of activation of a surface of a composite material before painting or bonding can be similarly quantified as a strain amount of the test piece by a residual compressive stress. As a matter of course, a new non-standard test piece may also be used.

FIG. 6 shows an example of results of good or bad in a degree of activation of a blast treated surface of a sample of CFRP with changing blast treatment conditions.

As shown in FIG. 6, blast treatment of a sample of CFRP was tested with changing a distance between the nozzles 5 and the sample of CFRP, the number of injecting media, and a pressure of compressed air for injecting the media. As other blast treatment conditions, the kind of the media is white alumina whose nominal designation number, showing an average particle size (a particle size range), is No. 100 (#100), and an injection amount of the media is 1 kg/minute. The average particle size of white alumina #100 is from 106 μm to 150 μm.

Blast treatment has been performed for a platy CFRP having concavity and convexity, with swinging each of the two nozzles 5, disposed as exemplified in FIG. 1, in the horizontal direction in a period of 50 Hz like a wiper, along an arc locus formed on a sector whose central angle is 51 degrees and radius is 324 mm, and moving the two nozzles 5 in the vertical direction, at a speed of 60 cm/minute. Therefore, the number of injecting media corresponds to the number of moving the nozzles 5 along the same locus.

The distance D between the two nozzles 5, disposed as exemplified in FIG. 1, is 560 mm. The two nozzles 5 have inclined inside so as to be line symmetric on the horizontal plane so that injection directions of media injected from the two nozzles 5 are orthogonal to each other on the horizontal plane. Therefore, the angle θ between each of the injection directions of the media and a straight line connecting between the two nozzles 5 on the horizontal plane is 45 degrees.

The distance between the nozzles 5 and the CFRP was considered as the distance between the straight line connecting the two nozzles 5 and the surface of the CFRP. Therefore, to be precise, an actual flying distance of the media injected from each of the nozzles 5, from each of the nozzles 5 to a collision position on the CFRP, is longer than the distance between the nozzles 5 and the CFRP. Specifically, in case that the distance between the nozzles 5 and the CFRP is 280 mm, the flying distance of the media from each of the nozzles 5 to the collision position on the CFRP becomes $280 \times 2^{1/2}$ mm since the locus of the center line of the radially injected media inclines at 45 degrees.

Each word "PASS" in FIG. 6 shows that non-negligible damage did not arise on the surface of the CFRP after the blast treatment while each word "NG" shows that the damage arose on the surface of the CFRP after the blast treatment and fibers were exposed.

According to FIG. 6, when the distance between the nozzles 5 and the sample of the CFRP is 280 mm, it can be confirmed that the CFRP was damaged under the conditions that the number of injecting the media is two times and the blast pressure is 0.6 [MPa], and also the conditions that the number of injecting the media is three times and the blast pressure is from 0.4 [MPa] to 0.6 [MPa]. Meanwhile, the distance between the nozzles 5 and the sample of the CFRP is partially 200 mm. In that case, it can be confirmed that the CFRP was damaged under the conditions that the number of injecting the media is two times and the blast pressure is from 0.4 [MPa] to 0.6 [MPa], and also the conditions that the number of injecting the media is three times and the blast pressure is from 0.3 [MPa] to 0.6 [MPa].

Figure 7:
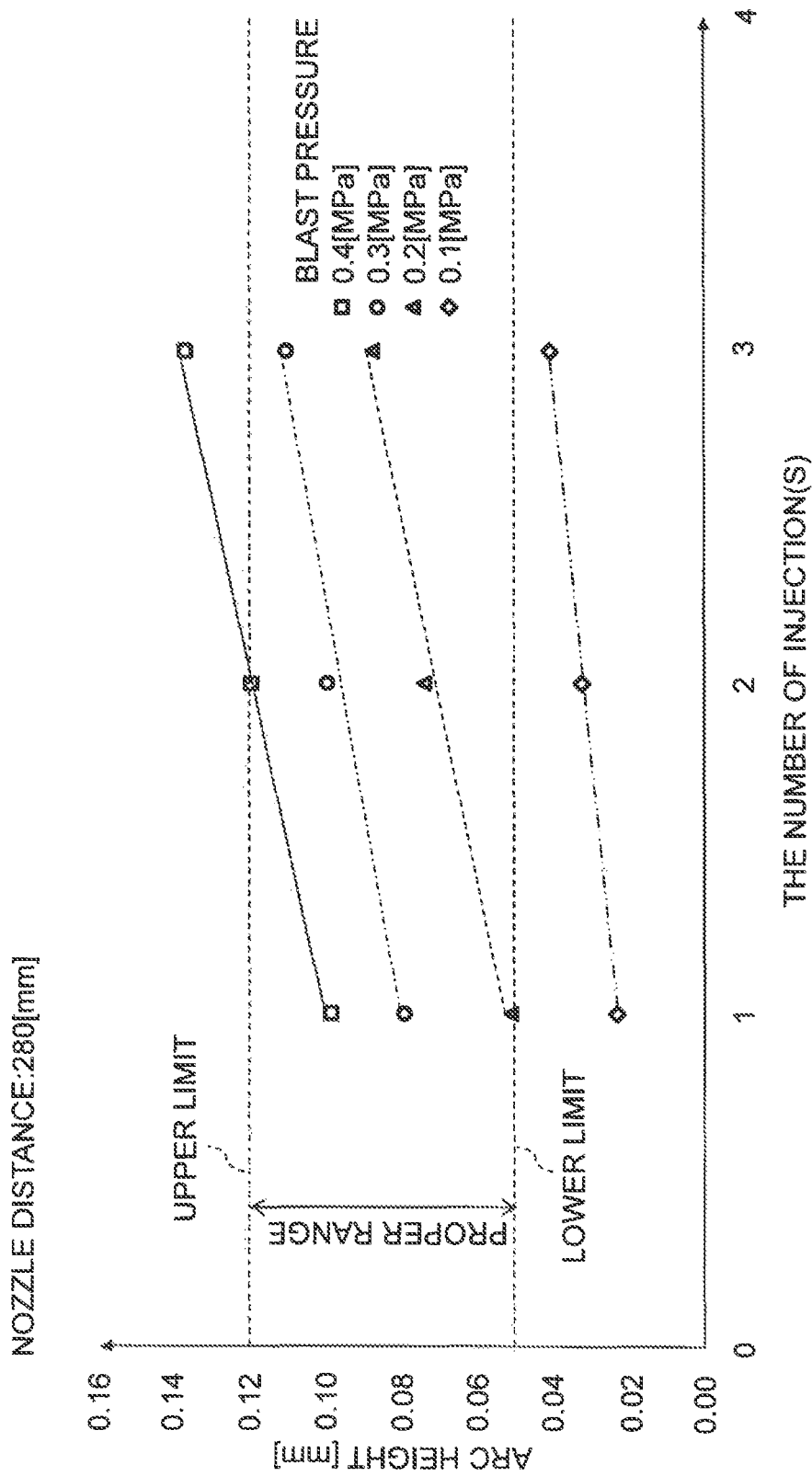
FIG. 7 is a graph showing an example of relating the blast treatment conditions and the good or bad in the degree of activation on the surface of the CFRP sample, shown in FIG. 6, with the arc heights of the T strip of the Almen strip.
Figure 8:
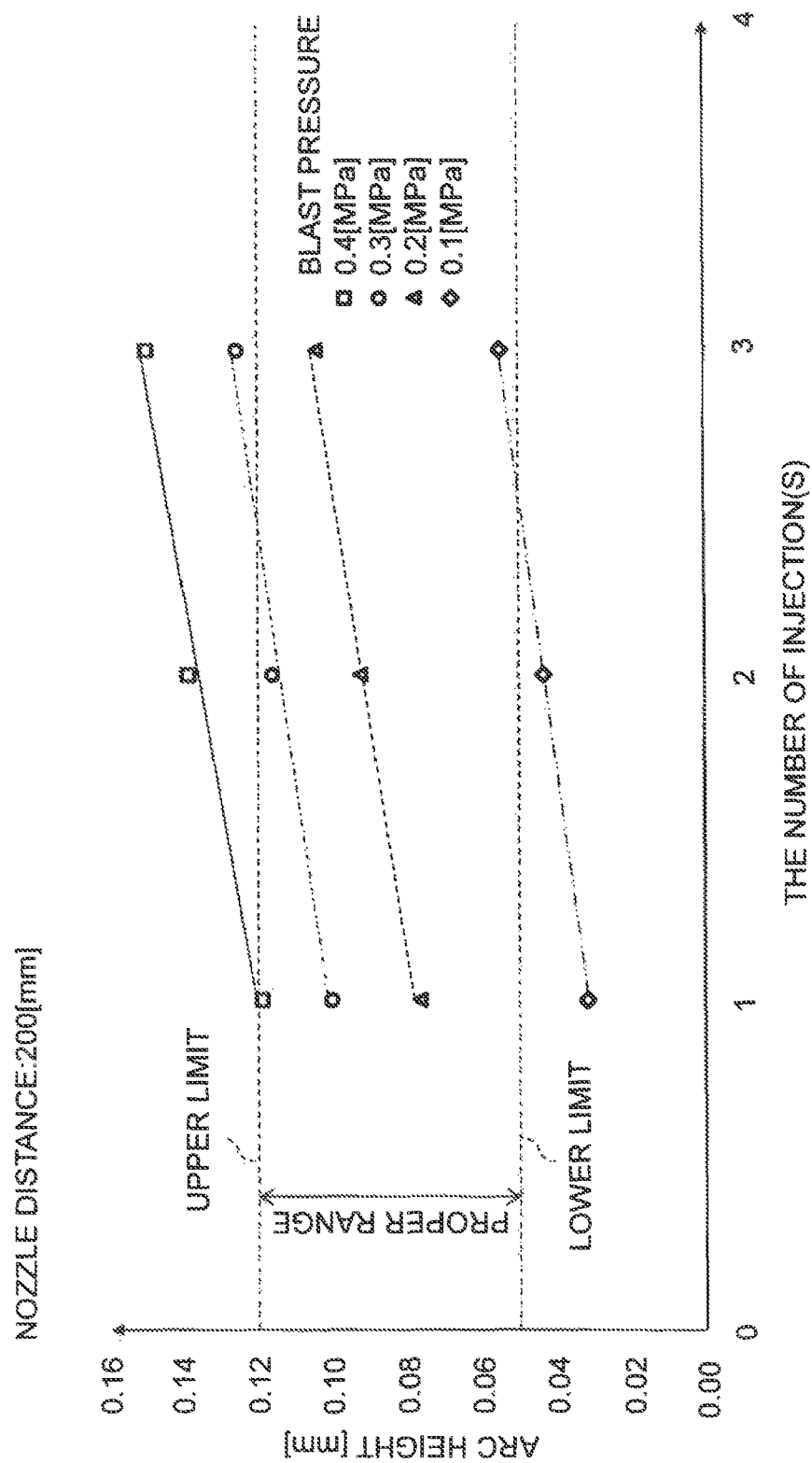
FIG. 8 is a graph showing another example of relating the blast treatment conditions and the good or bad in the degree of activation on the surface of the CFRP sample, shown in FIG. 6, with the arc heights of the T strip of the Almen strip.

FIG. 7 is a graph showing an example of relating the blast treatment conditions and the good or bad in the degree of activation on the surface of the CFRP sample, shown in FIG. 6, with the arc heights of the T strip of the Almen strip 10. FIG. 8 is a graph showing another example of relating the blast treatment conditions and the good or bad in the degree of activation on the surface of the CFRP sample, shown in FIG. 6, with the arc heights of the T strip of the Almen strip 10.

In FIG. 7 and FIG. 8, each vertical axis shows the arc height [mm] of the T strip of the Almen strip 10, each horizontal axis shows the number of injecting the media, each square mark shows the arc height of the T strip in case that the blast pressure is 0.4 [MPa], each circle mark shows the arc height of the T strip in case that the blast pressure is 0.3 [MPa], each triangle mark shows the arc height of the T strip in case that the blast pressure is 0.2 [MPa], and each rhombus mark shows the arc height of the T strip in case that the blast pressure is 0.1 [MPa], respectively.

FIG. 7 shows the arc heights of the T strip of the Almen strip 10 in case that the distance between the nozzles 5 and the T strip is set to be 280 mm. Meanwhile, FIG. 8 shows the arc heights of the T strip of the Almen strip 10 in case that the distance between the nozzles 5 and the T strip is set to be 200 mm. As described above, since the two nozzles 5 incline inside by 45 degrees, the actual flying distance of the media is longer than the distance between the nozzles 5 and the T strip of the Almen strip 10.

When arc heights of the T strip of the Almen strip 10 are measured by performing blast treatment of the T strip under the blast treatment conditions same as those shown in FIG. 6, the plotted data sets are obtained as shown in FIG. 7 and FIG. 8. That is, the arc heights of the T strip corresponding to different combinations of blast treatment conditions can be obtained.

According to the results of the blast treatment for the sample of the CFRP, shown in FIG. 6, when the distance between the nozzles 5 and the CFRP sample is 280 mm, the CFRP was damaged under the blast treatment conditions that the number of injecting the media is three times and the blast pressure is 0.4 [MPa]. Therefore, when the distance between the nozzles 5 and the T strip of the Almen strip 10 is set to be 280 mm, the arc height corresponding to the blast treatment conditions that the number of injecting the media is three times and the blast pressure is 0.4 [MPa] can be considered to be an arc height corresponding to inappropriate blast treatment conditions.

Similarly, when the distance between the nozzles 5 and the sample of the CFRP is 200 mm, the CFRP was damaged under the blast treatment conditions that the number of injecting the media is two or three times and the blast pressure is 0.4 [MPa], and also the blast treatment conditions that the number of injecting the media is three times and the blast pressure is 0.3 [MPa]. Therefore, when the distance between the nozzles 5 and the T strip of the Almen strip 10 is set to be 200 mm, each of the arc heights corresponding to the blast treatment conditions that the number of injecting the media is two or three times and the blast pressure is 0.4 [MPa], and also the blast treatment conditions that the number of injecting the media is three times and the blast pressure is 0.3 [MPa] can be considered to be an arc height corresponding to inappropriate blast treatment conditions.

By relating such results of blast treatment tests of a composite material with arc heights, the upper limit of the arc height for making the blast treatment conditions appropriate can be obtained.

While only whether carbon fibers were exposed from the CFRP has been shown in FIG. 6 as the results of the blast treatment tests, it is also important to examine whether the surface of the CFRP was sufficiently activated, by measuring the surface roughness and observing the presence of paint peeling of the CFRP after the blast treatment. When blast treatment conditions under which a surface of a composite material, such as CFRP, is not sufficiently activated can be specified, the lower limit of arc height for making blast treatment conditions appropriate can be obtained.

A relation between a range of the arc height of the T strip of the Almen strip 10 and a range of an appropriate blast treatment condition was examined based on blast treatment tests of CFRP as described above. As a result, it was confirmed that the surface of the CFRP was not roughened enough and could not be sufficiently activated in case that the arc height was less than 0.05 mm. On the contrary, it was confirmed that the carbon fibers of the CFRP may have been damaged when the arc height of the T strip was more than 0.12 mm.

Therefore, when the T strip of the Almen strip 10 or a test piece, which can be considered to be substantially equivalent to the T strip, is used, cases where the arc height value of the T strip or the test piece, which can be considered to be substantially equivalent to the T strip, becomes from 0.05 mm to 0.12 mm can be considered as an appropriate range in degree of activation on the surface of the CFRP, as shown in FIG. 7 and FIG. 8. Then, the blast treatment conditions corresponding to the cases where the arc height value of the T strip or the test piece, which can be considered to be substantially equivalent to the T strip, becomes from 0.05 mm to 0.12 mm can be considered as conditions for making the degree of activation on the surface of the CFRP appropriate.

In case of using another test piece, an appropriate range of strain amount of the test piece can be obtained similarly. Then, blast treatment conditions corresponding to the appropriate range of the strain amount of the test piece can be considered as conditions for making a degree of activation on a surface of a composite material, before painting or bonding, appropriate.

In the examples shown in FIG. 6, FIG. 7 and FIG. 8, each arc height of the Almen strip 10 has been related with the number of injecting media used for blast treatment, a representative distance between the nozzles 5 and a composite material, and a pressure of compressed air for injecting the media. Therefore, the number of injecting the media, the representative distance between the nozzles 5 and the composite material, and the pressure of compressed air for injecting the media, which correspond to an appropriate range of the arc height, can be set as blast treatment conditions for making a degree of activation on a surface of a composite material appropriate.

Note that, relations between the arc height of the Almen strip 10 and other parameters of blast treatment conditions, such as a type of media, an injection amount of media per unit time, and a movement speed of the nozzles 5 may also be obtained by changing those parameters. Furthermore, a desired distance other than the distance between the nozzles 5 and a composite material may also be used as a representative value of an injection distance of media. Note that, the number of injecting media, a representative value of an injection distance of the media, and a pressure of compressed air for injecting the media are considered to be dominant parameters of blast treatment conditions, influencing the good or bad for a degree of activation on a surface of a composite material.

Therefore, it is preferable to obtain information showing a relation between a strain amount of a test piece, such as an arc height of the Almen strip 10, and a degree of activation on a surface of a sample of a composite material, as reference information, for every predetermined blast treatment conditions including at least one of the number of injecting media used for blast treatment, a representative value of an injection distance of the media, and a pressure of compressed air for injecting the media. The number of blast tests or time and effort can be reduced by limiting changed parameters to dominant parameters. In other words, the same appropriate range of deformation amount of a test piece can also be related with non-dominant parameters changing slightly.

As a specific example, in case of using white alumina #180 whose average particle size is from 53 μm to 90 μm, the same appropriate range of arc height as that in a case of using white alumina #100 may be able to be allocated when an acceptable range in degree of activation of a composite material is wide.

When blast treatment is performed by using alumina #100 as media, recovery efficiency improves due to the large weight, compared with a case of using alumina #180. Furthermore, in case of using alumina #100, a difference between the weight of media and the weight of resin dust dropping from a composite material, such as CFRP, by blast treatment becomes large, compared with the case of using alumina #180. Therefore, it becomes easy to separate impurities from media.

It is considered that using ceramic particles, whose average particle size is from 106 µm to 150 µm, as media makes it possible to obtain advantages similar to that in case of using alumina #100 as media since a difference in specific gravity between the ceramic particle and a resin is large. Therefore, using ceramic particles, whose average particle size is from 106 µm to 150 µm, as media is appropriate for reusing the media after blast treatment. For these reasons, it is preferable to relate an appropriate range of strain amount of a test piece, in case of using ceramic particles, such as alumina #100, whose average particle size is from 106 µm to 150 µm, with blast treatment conditions and store the related appropriate range of strain amount of the test piece as reference information.

A relation between strain amounts of a test piece and blast treatment conditions may also be obtained as a function as well as a table for converting each strain amount of the test piece into blast treatment conditions, like the plotted data shown in FIG. 7 and FIG. 8. In case of obtaining a relation between strain amounts of a test piece and blast treatment conditions as a function, what is necessary is to perform interpolation processing and/or curve fitting based on plotted data.

When a range of strain amount of a test piece corresponding to an appropriate range of parameter of blast treatment conditions is stored as reference information in the reference information storage part 4, blast treatment conditions can be set with referring to the reference information in the blast treatment condition setting part 3. The blast treatment conditions can be set automatically or semi-automatically in the blast treatment condition setting part 3 with referring to the reference information.

When blast treatment conditions are automatically set, a parameter or parameters of the blast treatment conditions corresponding to the middle value of an appropriate range of strain amount of a test piece can be automatically set, for example. The blast treatment conditions have a plurality of parameters. Therefore, when partial parameters have been manually set by operating the input circuit 3A, the other unset parameters may be automatically set based on the reference information.

When blast treatment conditions are semi-automatically set, diverse user interfaces can be prepared. Examples of the user interface include: a user interface displaying candidate values of at least one desirable parameter for setting the blast treatment conditions on the display 3B so that a user can select a value of the parameter by operating the input circuit 3A; a user interface displaying an appropriate range of at least one desirable parameter for setting the blast treatment conditions on the display 3B so that a value of the parameter can be designated by operating the input circuit 3A to input a numerical value or move a scroll bar; a user interface displaying a value of a strain amount of a test piece corresponding to blast treatment conditions set by operating the input circuit 3A; a user interface displaying candidates of blast treatment conditions corresponding to a strain amount of a test piece designated by operating the input circuit 3A; and a user interface sounding an alarm when a strain amount of a test piece corresponding to blast treatment conditions designated by operating the input circuit 3A is out of a range of strain amount of the test piece corresponding to appropriate blast treatment conditions.

Meanwhile, all blast treatment conditions may be manually set. In that case, blast treatment of a composite material can be performed using the conventional blast treatment device which does not have the reference information storage part 4. In such a case, reference information for setting blast treatment conditions can also be stored in writing or in an independent storage device so that the reference information can be referred to. Thereby, it becomes possible to set blast treatment conditions using an existing blast treatment device, similarly to a case of setting blast treatment conditions by the blast treatment device 1 shown in FIG. 1.

(Operation and Action)

Next, a flow of blast treatment of the workpiece W by the blast treatment device 1 will be described.

Figure 9:
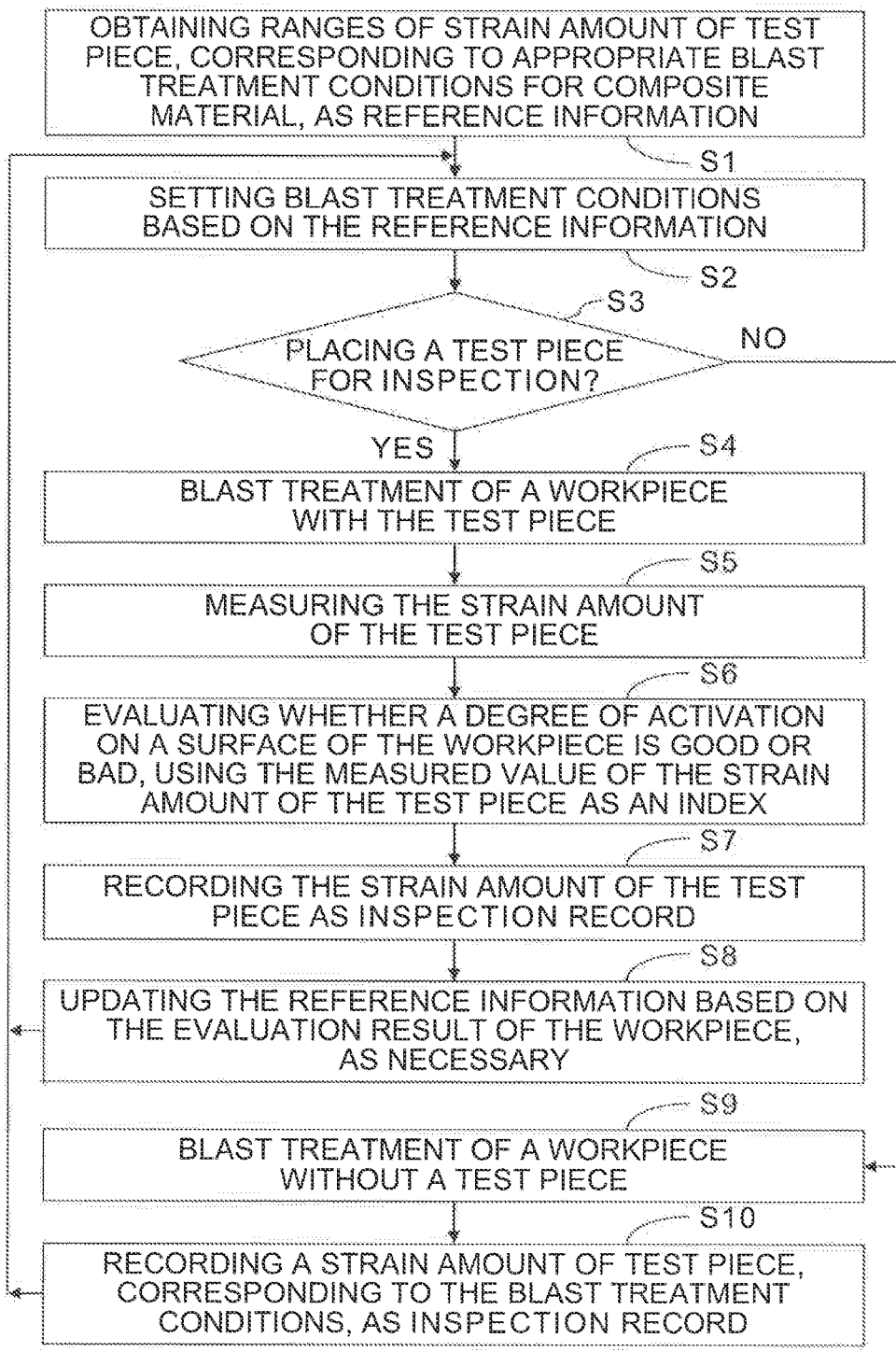
FIG. 9 is a flow chart showing an example of flow of blast treatment by the blast treatment device shown in FIG. 1.

FIG. 9 is a flow chart showing an example of flow of blast treatment by the blast treatment device 1 shown in FIG. 1.

Firstly, in step S1, reference information showing a relation between strain amounts of a test piece caused by blast treatment under predetermined combinations of blast treatment conditions and degrees of activation on a surface of a sample of a composite material by blast treatment, for activating the surface before painting or bonding, under the predetermined combinations of blast treatment conditions is obtained by blast treatment tests. Then, a range of strain amount of the test piece corresponding to appropriate blast treatment conditions for the composite material, such as the number of injecting media and a blast pressure, is specified. Specifically, a range of arc height of the Almen strip 10 corresponding to appropriate parameters of blast treatment conditions is specified as exemplified in FIG. 7 or FIG. 8.

The specified range of the strain amount of the test piece corresponding to the appropriate blast treatment conditions for the composite material is stored as reference information in the reference information storage part 4. When the reference information is stored in the reference information storage part 4, it becomes possible to set appropriate blast treatment conditions to perform blast treatment of a workpiece W made with a composite material, such as CFRP, to be a target of the blast treatment actually.

For starting the blast treatment of the workpiece W, the blast treatment conditions are set by the blast treatment condition setting part 3, with referring to the reference information, in step S2. Specifically, the blast treatment conditions for the composite material, which is a target of the blast treatment, are set based on the reference information so that the degree of activation on the surface of the composite material is within an appropriate range.

As a specific example, the blast treatment conditions are set so that a value of arc height caused by the blast treatment of a T strip of the Almen strip 10 or a test piece, which can be considered to be substantially equivalent to the T strip, becomes from 0.05 mm to 0.12 mm.

Next, in step S3, it is determined whether to place a test piece for inspecting the composite material after the blast treatment. In case of placing the test piece for inspecting the composite material after the blast treatment, the blast treatment is performed for the workpiece W with the placed test piece, in step S4. Thereby, a blast treated product is manufactured.

That is, the blast treatment is performed for the test piece and the workpiece W under the same blast treatment conditions. Specifically, the blast treatment is performed for both the test piece and the workpiece W under the blast treatment conditions which are set so as to make a degree of activation on a surface of a composite material within an appropriate range, e.g., such blast treatment conditions that a value of arc height caused by performing the blast treatment of a T strip of the Almen strip 10 or a test piece, which can be considered to be substantially equivalent to the T strip, becomes from 0.05 mm to 0.12 mm. When the blast treatment of all surfaces of the composite material, which are targets of the blast treatment, is completed, the blast treated product can be obtained as the composite material after the blast treatment.

When the blast treatment is completed, a strain amount of the test piece after the blast treatment is measured in step S5. When the strain amount of the test piece is measured, the workpiece W after the blast treatment, which is the blast treated product, can be inspected using a measured value of the strain amount of the test piece as an index. Thus, in step S6, the measurement result of the strain amount of the test piece is compared with the reference information. Then, it is evaluated whether the degree of activation on the surface of the workpiece W after the blast treatment is within an appropriate range, based on the measurement result of the strain amount of the test piece and the reference information.

Specifically, when the measurement result of the strain amount of the test piece is within the range of strain amount of the test piece corresponding to the appropriate blast treatment conditions for the composite material, the degree of activation on the surface of the workpiece W can be determined to be within the appropriate range. As a more specific example, when the arc height value of the T strip of the Almen strip 10 is within the range from 0.05 mm to 0.12 mm, the degree of activation on the surface of the composite material, such as CFRP, can be determined to be within the appropriate range.

On the contrary, when the measurement result of the strain amount of the test piece is out of the range of the strain amount of the test piece corresponding to the appropriate blast treatment conditions for the composite material, the degree of activation on the surface of the workpiece W can be determined to be out of the appropriate range. As a more specific example, when the arc height value of the T strip of the Almen strip 10 is out of the range from 0.05 mm to 0.12 mm, the degree of activation on the surface of the composite material, such as CFRP, can be determined to be out of the appropriate range.

The measurement result of the strain amount of the test piece, used for a quantitative evaluation of the degree of activation on the surface of the workpiece W as described above, can be recorded as an inspection record of the workpiece W after the blast treatment, in step S7. For example, the deformed test piece itself can also be attached to the workpiece W as an inspection record, so as to be delivered to the post-process, besides recording the measured value of the strain amount of the test piece. Thereby, the quality of the workpiece W after the blast treatment can be avouched. In addition, when measured values of strain amounts of test pieces are accumulated, a performance evaluation of the blast treatment device 1 can also be performed by examining dispersion of the strain amounts of the test pieces.

The blast treatment of the test piece and the workpiece W has been performed under the blast treatment conditions set based on the reference information. Therefore, when it is evaluated that the degree of activation on the surface of the workpiece W is not appropriate, the reference information referred to for setting the blast treatment conditions is considered to be inappropriate. Such a case may result from factors, such as errors between control values of the blast treatment conditions and the actual blast treatment conditions, and dispersion in the characteristics of the workpiece W.

Thus, in step S8, the reference information can be updated based on the evaluation result of the workpiece W, as necessary. Thereby, a possibility that blast treatment conditions are set again to inappropriate conditions can be reduced.

Then, for a new workpiece W, the blast treatment and the evaluation of the workpiece W from step S2 to step S8 can be repeated similarly. Furthermore, repeating update of the reference information based on the evaluation result of the workpiece W makes it possible to make the reference information preferred and optimize the reference information. When appropriate blast treatment conditions can always be set by making the reference information preferred and optimizing the reference information, an inspection of a workpiece W by measuring a strain amount of a test piece can be omitted.

In such a case, it can be determined not to place a test piece for inspecting the composite material after the blast treatment, in step S3. In that case, the blast treatment of the workpiece W, which is a target of the blast treatment, is performed without placing a test piece, in step S9. In this case, a strain amount of a test piece corresponding to the blast treatment conditions may also be recorded as an inspection record of the workpiece W after the blast treatment, in step S10, as necessary.

As a matter of course, after blast treatment of a workpiece W without placing a test piece, blast treatment of a workpiece W may also be performed again with placing a test piece. Furthermore, by measuring a strain amount of a set test piece, both a measurement result of the strain amount of the test piece and a strain amount of a test piece corresponding to blast treatment conditions may also be recorded as an inspection record of at least one of a workpiece W and the blast treatment device 1.

That is, the blast treatment device 1 and the blast treatment method as described above are device and method which can set conditions for blast treatment of a composite material, for activating a surface before painting or bonding, to appropriate conditions, based on strain amounts of test pieces obtained by previously performed blast treatment of the test pieces with changing the conditions.

(Effects)

Therefore, according to the blast treatment device 1 and the blast treatment method as described above, a degree of activation on a surface of a composite material after blast treatment can be quantified using a strain amount of a test piece as an index. Namely, a degree of activation on a surface of a composite material can be expressed by a numerical value.

Therefore, blast treatment conditions can be made preferred and an inspection accuracy after blast treatment can be improved. As a result, damage of a workpiece due to excess blast treatment or, in contrast, paint peeling resulting from insufficient blast treatment can be prevented. In addition, blast treatment conditions can be determined uniformly with high accuracy. Therefore, dispersion in degrees of activation on surfaces of composite materials can be reduced, thereby qualities of blasted products and painted products can be guaranteed.

In addition, when blasted products are inspected using strain amounts of test pieces as indexes, dispersion of the blasted products can also be evaluated. Furthermore, processing ability of the blast treatment device 1 can also be evaluated.

While certain implementations have been described, these implementations have been presented by way of example only, and are not intended to limit the scope of the invention. Indeed, the novel methods and systems described herein may be embodied in a variety of other forms; furthermore, various omissions, substitutions and changes in the form of the methods and systems described herein may be made without departing from the spirit of the invention. The accompanying claims and their equivalents are intended to cover such forms or modifications as would fall within the scope and spirit of the invention.

What is claimed is:

1. A blast treatment method comprising:
   setting a blast treatment condition for a composite material, the composite material being a target of blast treatment for activating a surface before painting or bonding, to make a degree of activation on a surface of the composite material within an appropriate range, based on reference information, the reference information showing a relation between a strain amount of a test piece caused by blast treatment under a predetermined blast treatment condition and a degree of activation on a surface of a sample of a composite material by blast treatment, for activating the surface of the sample before painting or bonding, under the predetermined blast treatment condition; and
   manufacturing a blast treated product by blast treatment of the composite material, the composite material being the target of the blast treatment, under the blast treatment condition set to make the degree of activation within the appropriate range.

2. The blast treatment method according to claim 1, wherein the reference information shows a relation between a strain amount of a test piece corresponding to each predetermined blast treatment condition and the degree of activation on the surface of the sample, the each predetermined blast treatment condition including at least one of an injecting number of media used for the blast treatment, a representative value of an injection distance of the media, and a pressure of compressed air for injecting the media.

3. The blast treatment method according to claim 1, wherein an Almen strip or a test piece substantially equivalent to an Almen strip is used as the test piece, and an arc height value of the Almen strip or the test piece is the strain amount.

4. The blast treatment method according to claim 1, wherein a T strip of an Almen strip or a test piece substantially equivalent to a T strip of an Almen strip is used as the test piece, a carbon fiber reinforced plastic is used as the sample, and an arc height value of the T strip or the test piece is from 0.05 mm to 0.12 mm as the degree of activation on a surface of the carbon fiber reinforced plastic.

5. The blast treatment method according to claim 1, further comprising:
   recording the strain amount of the test piece, corresponding to the set blast treatment condition, as an inspection record of at least one of the composite material after the blast treatment and a blast treatment device used for the blast treatment.

6. The blast treatment method according to claim 1, wherein ceramic particles of which an average particle size is from 106 μm to 150 μm are used as media for the blast treatment.

7. A blast treatment method comprising:
   manufacturing a blast treated product by blast treatment of a test piece and a composite material, the composite material being a target of the blast treatment for activating a surface before painting or bonding, the test piece and the composite material being blast treated under a common blast treatment condition;
   measuring a strain amount of the test piece after the blast treatment; and
   evaluating whether a degree of activation on a surface of the composite material after the blast treatment is within an appropriate range, based on a measurement result of the strain amount and reference information,
   wherein the reference information shows a relation between a strain amount of the test piece or another test piece caused by blast treatment under a predetermined blast treatment condition and a degree of activation on a surface of a sample of a composite material by blast treatment, for activating the surface of the sample before painting or bonding, under the predetermined blast treatment condition.

8. The blast treatment method according to claim 7, further comprising:
   recording the measurement result of the strain amount as an inspection record of at least one of the composite material after the blast treatment and a blast treatment device used for the blast treatment.

9. The blast treatment method according to claim 7, wherein the reference information shows a relation between a strain amount of a test piece corresponding to each predetermined blast treatment condition and the degree of activation on the surface of the sample, the each predetermined blast treatment condition including at least one of an injecting number of media used for the blast treatment, a representative value of an injection distance of the media, and a pressure of compressed air for injecting the media.

10. The blast treatment method according to claim 7, wherein an Almen strip or a test piece substantially equivalent to an Almen strip is used as the test piece, and an arc height value of the Almen strip or the test piece is the strain amount.

11. The blast treatment method according to claim 7, wherein a T strip of an Almen strip or a test piece substantially equivalent to a T strip of an Almen strip is used as the test piece, a carbon fiber reinforced plastic is used as the sample, and an arc height value of the T strip or the test piece is from 0.05 mm to 0.12 mm as the degree of activation on a surface of the carbon fiber reinforced plastic.

12. The blast treatment method according to claim 7, wherein ceramic particles of which an average particle size is from 106 μm to 150 μm are used as media for the blast treatment.

13. A blast treatment method comprising:
    setting a blast treatment condition under which an arc height value of a T strip of an Almen strip or a test piece substantially equivalent to a T strip of an Almen is from 0.05 mm to 0.12 mm by blast treatment; and
    manufacturing a blast treated product by blast treatment of a composite material, the composite material being a target of the blast treatment for activating a surface before painting or bonding, under the blast treatment condition.

14. The blast treatment method according to claim 13, wherein ceramic particles of which an average particle size is from 106 μm to 150 μm are used as media for the blast treatment.

15. A blast treatment device comprising:

storage circuitry storing reference information showing a relation between a strain amount of a test piece caused by blast treatment under a predetermined blast treatment condition and a degree of activation on a surface of a sample of a composite material by blast treatment for activating the surface before painting or bonding under the predetermined blast treatment condition;

processing circuitry configured to set a blast treatment condition for a composite material, the composite material being a target of blast treatment for activating a surface before painting or bonding, to make a degree of activation on the surface of the composite material, the composite material being the target of the blast treatment, within an appropriate range, based on the reference information; and blasting structure that performs blast treatment of the composite material, the composite material being the target of the blast treatment, under the blast treatment condition determined to make the degree of activation within the appropriate range.

* * * * *